(12) United States Patent
Santini et al.

(10) Patent No.: US 7,838,551 B2
(45) Date of Patent: Nov. 23, 2010

(54) PROCESS FOR THE PREPARATION OF CONCENTRATED, STERILE INJECTABLE SOLUTIONS CONTAINING DOCETAXEL

(75) Inventors: Marco Antônio Santini, Juiz de Fora (BR); Antônio Machado, Juiz de Fora (BR); Aurélio Maranduba, Juiz de Fora (BR); Eneida Guimarães, Juiz de Fora (BR); Marcio Santiago Junior, Juiz de Fora (BR); Maria Silva, Juiz de Fora (BR)

(73) Assignees: Quiral Quimica do Basil S.A., Sao Pedro (BR); Biorganica LTDA., Sao Pedro (BR)

( * ) Notice: Subject to any disclaimer, the term of this patent is extended or adjusted under 35 U.S.C. 154(b) by 374 days.

(21) Appl. No.: 10/582,385

(22) PCT Filed: Dec. 10, 2004

(86) PCT No.: PCT/BR2004/000242

§ 371 (c)(1),
(2), (4) Date: Aug. 15, 2007

(87) PCT Pub. No.: WO2005/061474

PCT Pub. Date: Jul. 7, 2005

(65) Prior Publication Data

US 2008/0051450 A1    Feb. 28, 2008

(30) Foreign Application Priority Data

Dec. 12, 2003    (BR) .............................. PI0305824-7
Dec. 8, 2004    (BR) .............................. PI0405797-0

(51) Int. Cl.
*A61K 31/335*    (2006.01)
*A61K 31/34*    (2006.01)

(52) U.S. Cl. ........................ 514/449; 514/471; 514/408

(58) Field of Classification Search .................. None
See application file for complete search history.

(56) References Cited

U.S. PATENT DOCUMENTS 5,475,120 A    12/1995    Rao (Continued)

FOREIGN PATENT DOCUMENTS

| BR | PI 9508739-3 A | 10/1997 |
| EP | 1348430 A1 | 10/2003 |
| EP | 1694660 B1 | 8/2009 |
| WO | WO 92/09589 A1 | 6/1992 |
| WO | WO-96/22984 A1 | 8/1996 |
| WO | WO-0236582 A1 | 5/2002 |

OTHER PUBLICATIONS

Ringel, I., et al., "Taxol is Converted to 7-Epitaxol, a Biologically Active Isomer, in Cell Culture Medium," J. Pharma. and Experimental Therapeutics, vol. 242, No. 2, pp. 692-698 (1987).

(Continued)

*Primary Examiner*—Robert A Wax
*Assistant Examiner*—Melissa S Mercier
(74) *Attorney, Agent, or Firm*—Birch, Stewart, Kolasch & Birch, LLP

(57) ABSTRACT

This invention describes a process for the production of ANHYDROUS active pharmaceutical ingredients (APIs); a process for the preparation of HYDRATED active pharmaceutical ingredients, a process for the preparation of sterile and stable injectable solutions, and their use, more specifically, APIs which are taxane derivatives, especially (2R,3S) 4-acetoxy-2-α-benzoyloxy-5β-20-epoxy-1,7-β-10-β-tri-hydroxy-9-oxo-tax-11-en-13α-il 3-tert-butoxy carbonylamino-2-hydroxy-3-phenylpropionate (I); 4-acetoxy-2-α-benzoyloxy-5-β-20-epoxy-1,7β-10-β-tri-hidroxy-9-oxo-tax-11-en-13α-il (2R,3S) 3-benzoylamino-2-hydroxy-3-phenylpropionate (II), and particularly 4-acetoxy-2-α-benzoyloxy-5β-20-epoxy-1, 7-β-10-β-tri-hidroxy-9-oxo-tax-11-en-13α-il (2R,3S) 3-tert-butoxycarbonylamino-2-hydroxy-3-phenylpropionate tri-hydrate (III).

13 Claims, 1 Drawing Sheet

U.S. PATENT DOCUMENTS

| | | | |
|---|---|---|---|
| 5,476,954 A | | 12/1995 | Bourzat et al. |
| 5,504,102 A | | 4/1996 | Agharkar et al. |
| 5,698,582 A | * | 12/1997 | Bastart et al. ............ 514/449 |
| 5,733,888 A | | 3/1998 | Carver et al. |
| 5,808,113 A | | 9/1998 | Murray et al. |
| 6,002,025 A | | 12/1999 | Page et al. |
| 6,022,985 A | | 2/2000 | Authelin et al. |
| 6,040,330 A | * | 3/2000 | Hausheer et al. ............ 514/408 |
| 7,435,726 B2 | * | 10/2008 | Zeldis et al. ............ 514/183 |
| 2003/0158249 A1 | * | 8/2003 | Chi et al. ............ 514/449 |
| 2004/0116720 A1 | * | 6/2004 | Sharma et al. ............ 549/510 |

OTHER PUBLICATIONS

Szebeni, J., et al., "Complement Activation by Cremophor EL as a Possible Contributor to Hypersensitivity to Paclitaxel: an In Vitro Study," J. Natl. Cancer Institute, vol. 90, No. 4, pp. 300-306 (1998).

Kraemer, I., "Stabiilty of new and old docetaxel formulation," Johannes Gutenerg Univ., Mainz, Germany, Pharm Ztg, vol. 145, pp. 32-34 (2000).

Cresteil, T., et al., "Regioselective Metabolism of Taxoids by Human CYP3A4 and 2C8: Structure-Activity Relationship," Drug Metab. and Disposition, vol. 30, No. 4, pp. 438-445 (2002).

Wahl, A., et al., "Rearrangement Reactions of Taxanes: Structural Modifications of 10-Deacetylbaccatine III.," Tetrahedron, vol. 48, No. 34, pp. 6965-6974 (1992).

van Zuylen, L., et al., "Role of formulation vehicles in taxane pharmacology," Investigational New Drugs, vol. 19, pp. 125-141 (2001).

Samaranayake, G., et al., "Modified Taxols. 5.[1] Reaction of Taxol with Electrophilic Reagents and Preparation of a Rearranged Taxol Derivative with Tubulin Assembly Activity," J. Org. Chem., vol. 56, No. 17, pp. 5114-5119 (1991).

EPO Office Action issued Jun. 19, 2007.
EPO Office Action issued Feb. 13, 2008.
EPO Office Action issued Jul. 30, 2008.
EPO Office Action issued Aug. 20, 2008.
EPO Communication re Intent to Grant Patent issued Feb. 10, 2009.
EPO Decision to Grant Patent issued Mar. 12, 2009.

* cited by examiner

PROCESS FOR THE PREPARATION OF CONCENTRATED, STERILE INJECTABLE SOLUTIONS CONTAINING DOCETAXEL

This application is the National Stage of International Application PCT/BR2004/000242 filed Dec. 10, 2004, which claims priority under 35 USC §119(a)-(d) of Brazilian Application No. PI0405797-0 filed Dec. 8, 2004 and Brazilian Application No. PI0305824-7 filed Dec. 12, 2003.

SCOPE OF THE INVENTION

The present invention relates to a process for the preparation of API's, more specifically, taxane derivatives, especially (2R, 3S)4-acetoxy-2-a-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I) and 4-acetoxy-2-α-benzoyloxy-5-β-20-epoxy-1,7β-10-β-tri-hydroxy-9-oxo-tax-11-en-13α-yl (2R, 3S) 3-benzoylamino-2-hydroxy-3-phenylpropionate (II).

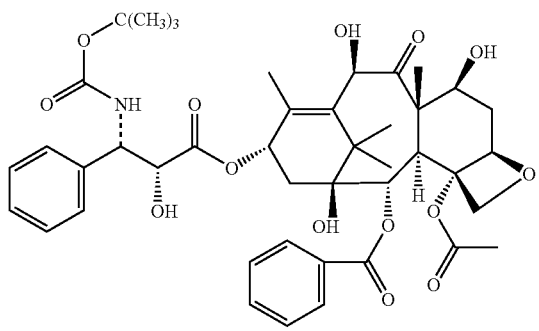

I

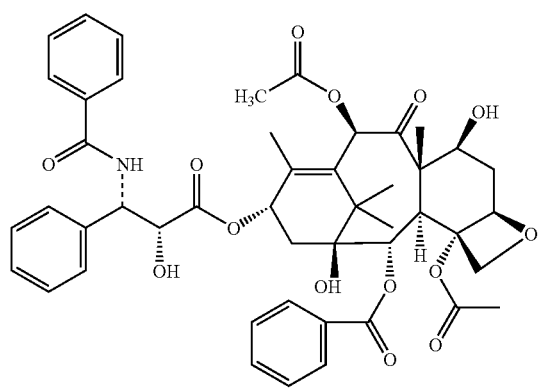

II

One innovative aspect of the present invention refers to a process particularly useful for obtaining anhydrous compounds which form hydrates, which prevents the removal of water by conventional processes such as drying under vacuum at elevated temperatures.

Another innovative aspect of the present invention refers to a process for the preparation of hydrated API's, more specifically taxane derivatives, especially the tri-hydrate of (2R, 3S) (2R, 3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (III).

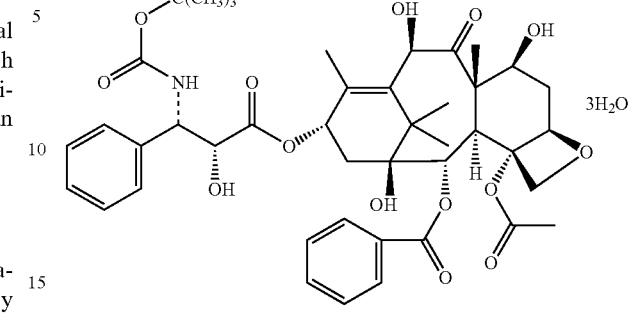

III

Yet another innovative aspect of the present invention is with respect to a process for the preparation of injectable solutions, which are sterile and stable, from the API's according to the processes herein described, which are useful in the treatment of disease or infirmity, including, but not limited to, neoplastic tumors and other conditions which respond to treatment with agents that inhibit the depolymerization of tubulins, for example, cancers of the breast, ovaries, lungs and others.

The solutions are obtained by way of dissolution of the active principle I, II or III indicated above, in an appropriate biocompatible vehicle, followed by filtration through a membrane having a porosity less than or equal to 0.45 μm; or, dissolution of the active principle I, II or III in an appropriate biocompatible vehicle, previously acidified with an organic or inorganic acid, followed by filtration through a membrane having a porosity less than or equal to 0.45 μm; or, dissolution of the active principle I, II or III in an appropriate biocompatible vehicle, posteriorly acidified, with an organic or inorganic acid followed by filtration through a membrane having a porosity less than or equal to 0.45 μm.

Lastly, the invention is also with respect to the stable pharmaceutical compositions thus obtained and the use of these compositions in the treatment of disease or infirmity, including, but not limited to, neoplastic tumors and other conditions which respond to treatment with agents that inhibit the depolymerization of tubulin, for example, cancers of the breast, ovaries, lungs and others.

PRIOR ART

The active principle (2R, 3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I), a taxane derivative obtained by chemical semi-synthesis, which presents anti-cancer and anti-leukemic properties.

There are various synthetic methods which lead to compound (I) as well as its tri-hydrate (III), for example, those cited in patent PCT-WO 92/09589 issued to Rhone-Poulenc Rorer S.A., U.S. Pat. No. 5,808,113 issued to Hauser Inc., and patent PCT-WO 96/01815, also issued to Rhone-Poulenc Rorer S.A.

The above mentioned compounds have demonstrated pharmacological activity against acute leukemia and solid tumors.

U.S. Pat. No. 5,504,102 issued to Briston-Myers Squibb describes a process for the preparation of polyethoxylated castor oil with low alkalinity and the use of this medium for the preparation of solutions containing antineoplastic agents.

Additionally, U.S. Pat. No. 5,698,582 issued to Rhone-Poulenc Rorer S. A. describes a process for the preparation of compositions containing taxane derivatives in a surfactant and the utility of these compositions for preparing perfusions.

Nonetheless, neither of these patents describe, nor do they suggest specifically, the use of anhydrous active principles in conjunction with polyethoxylated sorbitols which have been previously or posteriorly acidified for the preparation of sterile, injectable solutions, which confers additional stability to the compositions.

Brazalian patent application PI 950789-3A, whose priority is French patent FR 94 08479 issued to Rhone-Poulenc Rorer S. A., describes a process for the preparation of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (III), employing recrystallization from "a mixture of water and an aliphatic alcohol containing between 1 and 3 carbons, followed by drying the product obtained under pre-determined conditions of temperature, pressure and humidity."

This process presents various disadvantages. We call attention to the fact that this process suggests the prior purification of the (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate by chromatography.

Another disadvantage of this process resides in the fact that it is recommended that the solvents used in the cromatographic purification be removed by co-distillation with alcohol under reduced pressure which results in a "thick syrup whose agitation is difficult".

Yet another disadvantage of this invention lies in the fact that the process recommends refrigeration of the solution to 0° C. in order to obtain the best results.

Lastly, the cited process requires drying under vacuum at elevated temperatures in an atmosphere with controlled humidity, which requires costly and sophisticated equipment.

The patent in question also maintains that the tri-hydrate (III) obtained "presents clearly superior stability relative to the anhydrous product".

However, comparative studies realized in our laboratories have demonstrated that, when stored under adequate and controlled conditions, the anhydrous product (I) obtained by the processes claimed herein demonstrates a stability equal or superior to the tri-hydrate and, that under these conditions of storage, the produce does not re-hydrate to a significant degree.

It has been observed that utilization of the anhydrous product (I), cited above, confers an equal or superior stability to the pharmaceutical finished dosage form, which can be illustrated by stability studies of solutions of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I) in polyethoxylated sorbitol which has been previously or posteriorly acidified.

Brazilian patent application PI 9508789-3 cites as an example the addition of ascorbic acid in the preparation of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, via recrystallization, which involves a laborious and multi-step process, to confer additional stability to the API.

Therefore, patent application PI 9508789-3, cited here as a reference, neither describes nor anticipates in a manner obvious to a person skilled in the art, the process for the preparation of the anhydrous product (I), as claimed in the present invention, which may be obtained directly and with fewer experimental steps.

Furthermore, patent application PI9508789-3does not anticipate nor suggest in a manner obvious to a person skilled in the art, the additional stability conferred to pharmaceutical formulations by addition of an organic or inorganic acid as claimed in the present invention.

On the other hand, U.S. Pat. No. 5,698,582 describes a process for the preparation of solutions containing taxane derivatives in surfactants and the utilization of the same to prepare perfusions. This process requires that the active principle be first dissolved in ethanol, followed by addition of a surfactant and subsequent removal of the ethanol under vacuum.

This process involves several steps and manipulations which makes it complex, laborious and lengthy.

The process claimed in the present invention overcomes these disadvantages.

DETAILED DESCRIPTION OF THE INVENTION

In a first embodiment, the present invention is advantageous with respect to the state of the art in that it is not necessary to recrystallize the active principle (III), with the concomitant reduction in the overall yield of the process. The anhydrous active principle (I) may be obtained directly, in a single production step, resulting in considerable economy and a reduction in the number of steps.

In a second embodiment, the present invention also permits that, by use of the process described, (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I), of high purity, may be obtained in the form of an amorphous powder, which greatly facilitates its solubilization in biocompatible excipients. This results in the formation of solutions appropriate to be used directly in the confection of injectable pharmaceutical finished dosage forms without the addition of ethanol or other complementary excipients.

In a third embodiment, while the state of the art mentions that the addition of ascorbic acid during the recrystallization of the active principle (III) confers additional stability to it, an innovation particular to the present invention lies in the fact that it is advantageous to add a week acid during the preparation of pharmaceutical solutions of (I) and (III). This is neither mentioned nor suggested by the state of the art.

As such, additional stability may be conferred to the finished dosage forms by addition of a weak acid to the solution. Acids which may be employed include, but are not limited to: ascorbic, phosphoric, acetic, citric or tartaric acid.

A fourth embodiment of the present invention lies in the fact that it is not necessary to first solubilize the active principles in ethanol followed by the subsequent removal of the ethanol as described in U.S. Pat. No. 5,698,582.

As proposed herein, the compounds (I) and (II) may be solubilized directly in the vehicle utilized in the formulation without the necessity of adding a co-solvent.

In a fifth embodiment of the present invention, it is possible to obtain stable, sterile pharmaceutical presentations, absent of pyrogens, of small, medium and large volume, which are appropriate for administration after dilution, or for filling in ampoules, vials or other suitable recipients, which may be transported under adequate conditions for direct use in clinics and hospitals specialized in the treatment of cancer which possess installations for the dilution of cytostatic drugs.

The installations for the dilution of cytostatic drugs serve as a means to ensure the individualization of the treatment for the cancer patient and offer an economy in the administration of the prescribed medication.

In this context, it is indispensable that sterile, stable and apyrogenic injectable formulations be available, ready for administration in large volumes, ideally between 50 and 5,000 mL.

The solutions thus obtained may also be transported under adequate conditions and be filled into smaller recipients at another location.

In a sixth embodiment, the present invention also describes a process for the preparation of concentrated solutions of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate, (II) in polyethoxylated sorbitols.

The state of the art utilizes as a vehicle for the formulation of (II) a mixture of polyethoxylated castor oil, for example, Cremophor® EL or ELP and ethanol. It is well known that Cremophore® is responsible for various adverse reactions which requires premedication with anti-histamines, corticosteroids and/or $H_2$ antagonists.

Known commercial formulations also utilize considerable amounts of ethanol, which is responsible on many occasions for ethanol intoxication of the patient due to the large volume of product administered to achieve the desired therapeutic effect.

As such, the exclusion of polyethoxylated castor oil and ethanol from the compositions of the present invention presents considerable advantages from the patient point of view, and greatly reduce or eliminate the side-effects associated with these vehicles.

The process for the preparation of anhydrous API's according to the present invention, more specifically taxane derivatives, and especially (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I) and 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II) may be realized according to various procedures as will become evident.

In a seventh embodiment of the present invention, an hydrated sample of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I) is solubilized in a chemically inert solvent which forms an azeotrope with water. This solvent may be a linear or branched alcohol, an organic acid, a halogenated solvent, an aromatic solvent or another solvent of sufficient polarity capable of solubilizing the hydrated product. Preferably the solvent employed in the present invention is a short chain linear or branched alcohol.

The solution thus obtained is subjected to azeotropic distillation at a temperature between 20 and 200° C., and at a pressure between 1 and 800 mm Hg to remove the water of hydration. In the case of hydrated (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, the temperature is, preferably, below 40° C.

In an eighth embodiment of the present invention, the hydrated (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate may also be solubilized in a combination of two or more of the aforementioned solvents.

For example, these solvents may be a combination of a linear or branched alcohol, an organic acid, a halogenated solvent, an aromatic solvent or another solvent of sufficient polarity capable of solubilizing the hydrated product and capable of forming a binary, ternary or quaternary azeotrope with water.

In the case of hydrated (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, the proportion between the first and second solvent is on the order of between 1:2 to 1:90.

Afterwards, the azeotropic distillation may be carried out at a pressure between <0.001 and 780 mm Hg. In the case of hydrated (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, the pressure is preferentially between 0.1-100 mm Hg.

In a ninth embodiment of the present invention, impure (2R,3S) 4-acetoxy-2-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I) may be subjected to normal or reverse phase chromatography, employing a solvent or mixture of solvents among those routinely employed in the technique.

In the case of impure (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I), the stationary phase may be silica gel, alumina or cellulose, or chemically modified versions thereof, including but not limited to RP-C18, RP-C8, RP-pentafluorophenyl or RP-phenyl. The stationary phase employed is preferentially silica gel or RP-pentafluorophenyl.

In the case of normal phase chromatography, the solvents employed are esters, alcohols, alkanes, alkenes, alkynes, ethers, halogenated solvents, nitriles or mixtures thereof. It is understood that the technique of gradient elution may also be employed. In the present case concerning taxane derivatives, the solvents employed are preferentially mixtures of alkanes and esters.

In the case of reverse phase chromatography, the solvents employed are esters, alcohols, alkanes, alkenes, alkynes, ethers, halogenated solvents, nitriles, water, aqueous buffer solutions or mixtures thereof. It is understood that the technique of gradient elution may also be employed. In the present case concerning taxane derivatives, the solvents employed are preferentially mixtures of nitriles or a short chain linear alcohol and water in an acidic buffer.

After removal of the solvents, the anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate obtained may be used directly or submitted to one of the aforementioned processes for further purification and/or removal of water of hydration.

In a tenth embodiment of the present invention, a process for the formation of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate is described employing an anhydrous solvent, under controlled conditions, utilizing one or more of the processes cited in the state of the art, with reagents and raw materials of sufficient purity so as to lead directly to the formation of pure, anhydrous (I), after removal of the solvents.

In the case of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I), it is particularly advantageous to conduct the reaction in anhydrous tetrahydrofuran or anhydrous dioxane employing equimolar amounts of N-debenzoyl-10-desacetoxy paclitaxel >98% purity and di-tertbutyl-dicarbonate of >99%. Removal of the solvent and drying under vacuum affords directly anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in 98% yield.

In an eleventh embodiment of the present invention, we describe a process for the preparation of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (III), which may be realized via a simple and efficient technique.

To begin, (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I) is solubilized in a solvent which is chemically inert. This solvent may be a linear or branched alcohol containing between 1 and 8 carbons, an organic acid, an aliphatic or cyclic ether, a polar, aprotic solvent, a halogenated solvent, an aromatic solvent, a polyethoxylated sorbitol, lecithin or castor oil, or another solvent of adequate polarity to effect the complete solubilization of (I) and is capable of solubilizing, or is miscible with, at least 3 molar equivalents of water.

The solution so obtained is admixed with an amount of distilled water between 3 and 200,000 molar equivalents relative to (I). Crystallization is induced and the tri-hydrate (III) is isolated by means of conventional processes such as filtration, decantation or centrifugation.

As such, the steps necessary to realize the process according to the present invention are as follows:

a) (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (I) is solubilized in polyethoxylated sorbitol at a temperature between 1 and 60° C. with agitation. The quantity of polyethoxylated sorbitol employed is on the order of between 15 to 40 mL per gram of (2S,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. The polyethoxylated sorbitol employed is, preferably, but not exclusively, polysorbate 80.

b) The solution thus obtained is added to a quantity of distilled water and a co-solvent at ambient temperature to form a homogeneous mixture. The co-solvent employed is a linear alcohol containing between 1 and 8 carbons. The proportion of distilled water:alcohol is in the range of between 30 mL:1 mL to 300 mL:50 mL relative to each gram of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate present in the solution obtained in step a).

c) The mixture obtained is left to stand at room temperature during 48-240 h to permit the formation of crystals of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (III).

d) The crystals thus obtained are isolated by known techniques and washed with distilled water to remove vestiges of the solvents employed. Among the known techniques which can be used are filtration, decantation and centrifugation.

e) The crystals are then dried at ambient temperature in a dessicator over a dessicant, such as $P_2O_5$, concentrated $H_2SO_4$, NaOH, $Na_2SO_4$, $MgSO_4$ or $CaCl_2$, until reaching constant weight.

In relation to the state of the art, the present invention possesses diverse advantages which will be evident to persons skilled in the art, among which we may cite as most relevant, but not limited to:

a) the present invention avoids previous purification of the (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate by chromatography, the same being commercially available;

b) the process does not involve evaporation of solvents and avoids working at pressures below atmospheric;

c) the process does not result in the formation of a "thick syrup, whose stirring is difficult", which greatly facilitates the manipulation and handling of the solutions and simplifies the types of equipment required;

d) All of the steps of the process can be conducted at ambient temperatures, contrary to the state of the art which requires heating and refrigeration;

e) the process does not require vacuum drying neither control of humidity nor temperature during the drying operation.

In a twelfth embodiment of the present invention, there is also described the preparation of sterile, stable solutions of anhydrous or tri-hydrated, (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, (I) or (III), and also, 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II), in a biocompatible vehicle.

Appropriate vehicles include, but are not limited to, polyethoxylated sorbitols, and, preferentially polysorbate 80. The solutions are prepared by the slow addition of anhydrous or tri-hydrated (2R,3S) 4-acetoxy-2-α-benzoyloxy-5-20-epoxy-1,7-β-10-β-tri-hydroxy-9-oxo-tax-11-en-13α-yl 3-tert-butoxycarbonylamino-2-hydroxy-3-phenylpropionate, (I) or (III), or, 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II) to the vehicle with agitation, preferably, in an inert atmosphere, at a concentration between 1 and 100 mg of active ingredient on an anhydrous basis per mL polysorbate 80.

BRIEF DESCRIPTION OF THE FIGURES

As an illustrative point, schematic figures of the present invention are presented in which.

Figure 1:
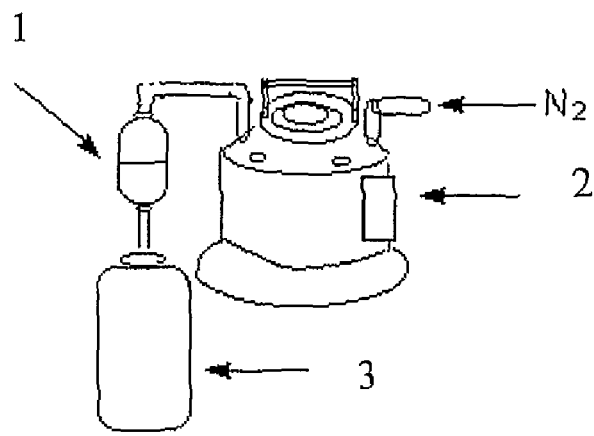
FIG. 1 refers to a schematic representation of the filtration process, as constituted in "Scheme 1"

With respect to the elements depicted in FIG. 1, number (1) represents a sterilizing membrane employed in the filtration with a porosity of 0.22 μm. The pressurized vessel is represented by number (2) and the recipient for the sterilized filtrate is represented by number (3). $N_2$ represents the pressure inlet for an inert gas such as nitrogen. The combination of these elements constitutes "Scheme 1".

Figure 2:
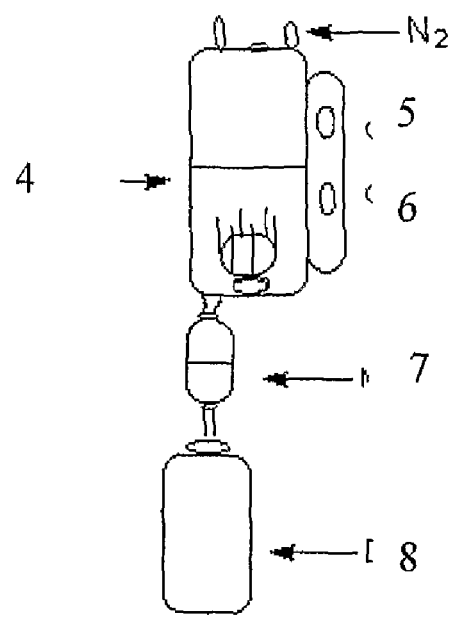
FIG. 2 refers to a schematic representation of the dissolution and filtration process as constructed in "Scheme 2".

With respect to FIG. 2, the following elements are depicted: reactor (4), temperature control (5), control for agitation (6), sterilizing filtration membrane (7), and the recipient for the sterilized filtrate (8). $N_2$ represents the pressure inlet for an inert gas such as nitrogen. The combination of these elements constitutes "Scheme 2".

According to scheme 1, FIG. 1, after complete solubilization of the active principle, the solution is transferred to a pressure vessel (2), filtered through the sterilizing membrane with a porosity of less than 0.45 μm, preferably 0.22 μm and filled into pyrogen free, sterile recipient(s) (3) in a sterile environment. The products thus obtained are stable for at least 18 months when stored between 2-8° C.

The preparation of sterile, stable solutions of anhydrous or tri-hydrated (2R,3S) 4-acetoxy-2-α-benzoyloxy-5β-20-epoxy-1,7-β-10-β-tri-hydroxy-9-oxo-tax-11-en-13β-yl 3-tert-butoxycarbonylamino-2-hydroxy-3-phenylpropionate, (I) or (III), and also, 4-acetoxy-2-α-benzoyloxy-5-β-20-epoxy-1,7β-10-β-tri-hydroxy-9-oxo-tax-11-en-13a-yl (2R,3S) 3-benzoylamino-2-hydroxy-3-phenylpropionate (II), in a biocompatible vehicle, may also be conducted in an alternative manner.

Appropriate vehicles include, but are not limited to, polyethoxylated sorbitols, and, preferably, polysorbate 80.

The solution is prepared directly in a stainless steel reactor (4), as shown in FIG. 2, by way of slow addition of the active principle (I), (II) or (III) to the vehicle with internal agitation, preferably under an inert atmosphere, at a concentration between 1 and 100 mg of active principle (on an anhydrous basis)/mL polysorbate 80.

According to scheme 2, after complete solubilization of the active principle, the solution is filtered directly through the sterilizing membrane (7) with a porosity of less than 0.45 μm, preferably 0.22 μm and collected in a sterile recipient (8) in a sterile environment. The solution thus obtained may be filled into pyrogen free, sterile vials, ampoules or other suitable recipient. The product thus obtained are stable for at least 18 months when stored between 2-8° C.

In a thirteenth embodiment of the present invention, the aforementioned vehicles may be previously or posteriorly acidified. It is advantageous to acidify the polysorbate 80 prior to the addition of the active principle with an organic, inorganic or mixture of acids, chemically compatible with the vehicle and active principle (I, II or III), including, but not limited to, phosphoric, acetic, citric, tartaric or ascorbic acids.

It is also advantageous to acidify the solution of the active principle in polysorbate 80 after the complete dissolution of the active principle (I), (II) or (III) with an organic, inorganic or mixture of acids, chemically compatible with the vehicle and active principle (I, II or III), including, but not limited to, phosphoric, acetic, citric, tartaric or ascorbic acids.

The solutions thus obtained are more stable than solutions which are not acidified. For the purpose of the present invention, the preferable acids to be employed are acetic or ascorbic. The pH may be adjusted between 3.0-6.5, preferably, between 3.5 and 4.5. Solutions prepared in this manner are stable for at least 24 months when stored between 2 and 8° C. (Tables 1 and 2).

TABLE 1

Comparative stability study of solutions of the tri-hydrate and anhydrous forms of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in polysorbate 80 with and without the addition of acid

| Time (months) | A % Docetaxel (tri-hydrate) | A % Docetaxel (anhydrous) | A % Docetaxel (anhydrous) with acetic acid | A % Docetaxel (anhydrous) With ascorbic acid |
|---|---|---|---|---|
| 0 | 100.10 | 99.87 | 100.04 | 99.98 |
| 3 | 100.07 | 99.72 | 99.89 | 99.72 |
| 6 | 99.23 | 99.02 | 99.03 | 99.34 |
| 12 | 97.41 | 97.21 | 98.98 | 98.79 |
| 18 | 96.23 | 96.09 | 98.13 | 98.02 |
| 24 | 94.14 | 90.09 | 97.67 | 97.48 |

Note 1:
All solutions were prepared at a concentration of 40 mg/mL, on an anhydrous basis, followed by filtration through a sterilizing membrane.
Note 2:
The acidified solutions were prepared from polysorbate 80 whose pH had been previously adjusted to between 3.5 and 4.5 by addition of the respective acids.
Note 3:
Samples were stored between 2 and 8 C.
Note 4:
Assay of docetaxel was performed by HPLC.

TABLE 2

Comparative stability study of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II) in Cremophor EL and polysorbate 80 with and without addition of ascorbic acid

| Time (months) | A % Paclitaxel (Cremophor EL) | A % Paclitaxel Anhydrous (polysorbate 80) | A % Paclitaxel Anhydrous (polysorbate 80 with ascorbic acid) |
|---|---|---|---|
| 0 | 100.08 | 100.55 | 100.30 |
| 3 | 99.46 | 100.10 | 100.20 |
| 6 | 99.04 | 99.81 | 99.99 |
| 12 | 96.46 | 97.02 | 97.90 |
| 18 | 92.10 | 93.05 | 97.01 |
| 24 | 85.16 | 89.84 | 94.97 |

Note 1:
All solutions were prepared at a concentration of 6 mg/mL on an anhydrous basis, followed by filtration through a sterilizing membrane.
Note 2:
The acidified solutions were prepared from polysorbate 80 whose pH had been previously adjusted to between 3.5 and 4.5 by addition of the respective acids.
Note 3:
Samples were stored between 2 and 8° C.
Note 4:
Assay of paclitaxel was performed by HPLC In a fourteenth and final embodiment of the present invention, the solutions obtained by the processes heretofore described are useful in the treatment of disease or infirmity, including, but not limited to, neoplastic tumors and other conditions which respond to treatment with agents that inhibit the depolymerization of tubulin, for example, cancers of the breast, ovaries, lungs and others.

EXAMPLE 1

Process for the removal of water of hydration by way of azeotropic distillation under vacuum A 1.00 g [1.16 mMol] sample of hydrated (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (6.27% water) was solubilized in 50 mL of reagent grade ethanol. The solution which was obtained was distilled under vacuum to remove the ethanol. The amorphous powder obtained was dried between 30 and 60° C. to constant weight, yielding 0.93 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate containing 0.10% water by KF titration.

EXAMPLE 2

Process for the removal of water of hydration by way of binary azeotropic distillation under vacuum A 1.00 g [1.16 mMol] sample of hydrated (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (6.27% water) was solubilized in 20 mL of ethanol. This was followed by the addition of 180 mL of toluene. The solution thus obtained was distilled under vacuum (20 mmHg/40° C.) to remove, firstly the ethanol. The azetrope formed between toluene and water was then distilled at 1 mmHg/28° C. Finally, the remainder of the toluene was removed and the amorphous powder obtained was dried at a temperature around 50° C. until constant weight, yielding 0.92 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate ester containing 0.12% water by KF titration.

EXAMPLE 3

Process for the preparation of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate by way of purification of impure (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate using column chromatography A 1.00 g sample of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, with a chromatographic purity of 97.7% (1.1% $H_2O$), prepared according to the method of Murray et al., was solubilized in 2 mL of dichloromethane. The solution obtained was applied to a column of silica gel 60 previously activated at 150° C. and eluted with a gradient of hexane:EtOAc varying from 80:20 to 20:80. The fractions containing pure (2R,3S) 4-acetoxy-2-α-benzoyloxy-5β-20-epoxy-1,7-β-10-β-tri-hydroxy-9-oxo-tax-11-en-13β-yl 3-tert-butoxycarbonylamino-2-hydroxy-3-phenylpropionate were collected and pooled and the solvent removed on a rotary film evaporator at a temperature between 35 and 75° C. at a pressure between 10 and 40 mm Hg. After drying, there were obtained 0.85 g of with a chromatographic purity of 99.34% and a water content of 1.2%.

EXAMPLE 4

Process for the preparation of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate using an anhydrous solvent as the reaction medium (This synthesis was realized utilizing a variation of the methodology described by Murray et al.).

Under an atmosphere of nitrogen, a round bottom flask was charged with 500 mL THF, previously distilled over sodium. 10 g [14.14 mMol] of 10-desacetyl-N-debenzoyl-paclitaxel (>99% chromatographic purity, <0.1% water by KF) was added in one portion. This was followed by the addition of 3.08 g [14.14 mMol] of di-tert-butyl-dicarbonate (Aldrich >99%). The reaction was monitored by TLC and, after complete consumption of the starting materials, the solvent was removed under vacuum. After drying the product under vacuum, 11.42 g (100%) of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate was isolated with a chromatographic purity of 99.28% (HPLC) and a water content of 0.08% (KF).

EXAMPLE 5

Preparation of the tri-hydrate (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate employing polysorbate 80, ethanol and water as solvents A 4.00 g sample of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (0.78% water, 98.8% chromatographic purity) was solubilized in 100 mL of polysorbate 80 with mechanical agitation. The solution thus obtained was added to a mixture containing 180 mL distilled water and 20 mL of absolute ethanol. The clear solution obtained was left at rest at ambient temperature. After two days, crystals (needles) began to form. After five days, the crystals that had formed were filtered, washed with distilled water, and dried between 20 and 30° C. in a dessicator over $P_2O_5$ until constant weight was obtained, yielding 3.97 g of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (III) (6.29% water by KF titration; the IR spectrum was identical to that of an authentic sample).

EXAMPLE 6

Preparation of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate employing polysorbate 80, n-butanol and water as solvents A 4.00 g sample of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (0.78% water, 98.8% chromatographic purity) was solubilized in 100 mL of Polysorbate 80 with mechanical agitation. The solution thus obtained was added to a mixture containing 160 mL distilled water and 30 mL of n-propanol.

The clear solution obtained was left at rest at ambient temperature. After two days, crystals (needles) began to form. After five days, the crystals that had formed were filtered, washed with distilled water, and dried between 20 and 30° C. in a dessicator over $P_2O_5$ until constant weight was obtained, yielding 3.67 g of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (III) (6.24% water by KF titration; the IR spectrum was identical to that of an authentic sample).

EXAMPLE 7

Preparation of the tri-hydrate of (2R,3S) 4-acetoxy-2-α-benzoyloxy-5β-20-epoxy-1,7-β-10-β-tri-hydroxy-9-oxo-tax- 11-en-13α-yl 3-tert-butoxycarbonylamino-2-hydroxy-3-phenylpropionate using the washings of production equipment used in the manufacture of sterile injectable solutions of (I) in polysorbate 80

To the sterilizing filtration system, consisting of a stainless steel, pressurized reactor, silicone rubber hoses and sterilizing filtration capsule with a porosity of 0.22 μm, and containing approximately 1.50 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in 36 mL of polysorbate 80, was added one liter of isopropanol. The resulting solution was collected and the alcohol removed under reduced pressure (20 mm Hg) at 40° C. The resulting solution was added to a mixture of 90 mL distilled water and 10 mL of ethanol with agitation. The clear solution which was obtained was left at rest at ambient temperature. After 2 days, crystals (needles) began to form. After 5 days, the crystals which had formed were filtered, washed with distilled water, and dried between 20 and 30° C. in a dessicator over $P_2O_5$ until constant weight, yielding 1.21 g of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate (6.21% water by KF titration; the IR spectrum was identical to that of an authentic sample).

EXAMPLE 8

Process for the preparation of a stable and sterile solution of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate ester in polysorbate 80 (with compressed air agitation)

In a beaker equipped with a helical compressed air agitator, under an atmosphere of $N_2$ was added 100 mL of polysorbate 80. This was followed by the slow addition of 4.00 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was transferred to a pressurized vessel and filtered through a 0.22 μm sterilizing membrane, in a sterile environment under pressure, and then filled in vials using customary procedures. The solution thus obtained was shown to be stable for 18 months when stored at temperatures between 2 and 8° C.

EXAMPLE 9

Process for the preparation of a stable and sterile solution of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in polysorbate 80 (using a stainless steel reactor)

In a stainless steel reactor equipped with an internal agitation system, under an atmosphere of $N_2$ was added 100 mL of polysorbate 80. This was followed by the slow addition of 4.00 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was filtered through a 0.22 μm sterilizing membrane coupled to the reactor, in a sterile environment under pressure, and then filled in vials using customary procedures. The solution thus obtained was shown to be stable for 18 months when stored at temperatures between 2 and 8° C.

EXAMPLE 10

Process for the preparation of a stable and sterile solution of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in previously acidified polysorbate 80 (with compressed air agitation)

In a beaker equipped with a helical compressed air agitator, under an atmosphere of $N_2$ was added 100 mL of polysorbate 80 which had been previous acidified with ascorbic acid to a pH of 3.9. This was followed by the slow addition of 4.00 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was transferred to a pressurized vessel and filtered through a 0.22 μm sterilizing membrane, in a sterile environment under pressure, and then filled with vials using customary procedures. The solution thus obtained was shown to be stable for 24 months when stored at temperatures between 2 and 8° C.

EXAMPLE 11

Process for the preparation of a stable and sterile solution of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylam. in previously acidified polysorbate 80 (using a stainless steel reactor)

In a stainless steel reactor equipped with an internal agitation system, under an atmosphere of $N_2$ was added 100 mL of polysorbate 80 which had been previously acidified with ascorbic acid to a pH of 3.9. This was followed by the slow addition of 4.00 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was filtered through a 0.22 μm sterilizing membrane coupled to the reactor, in a sterile environment under pressure, and then filled in vials using customary procedures. The solution thus obtained was shown to be stable for 24 months when stored at temperatures between 2 and 8° C.

EXAMPLE 12

Process for the preparation of a stable and sterile solution of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in posteriorly acidified polysorbate 80 (with compressed air agitation)

In a beaker equipped with a helical compressed air agitator, under an atmosphere of $N_2$ was added 100 mL of polysorbate 80. This was followed by the slow addition of 4.00 g of anhydrous (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was then acidified with ascorbic acid to a pH of 4.0. The resulting solution was transferred to a pressurized vessel and filtered through a 0.22 μm sterilizing membrane, in a sterile environment under pressure, and then filled in vials using customary procedures. The solution thus obtained was shown to be stable for 24 months when stored at temperatures between 2 and 8° C.

EXAMPLE 13

Process for the preparation of a stable and sterile solution of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in previously acidified polysorbate 80 (with compressed air agitation)

In a beaker equipped with a helical compressed air agitator, under an atmosphere of $N_2$ was added 100 mL of polysorbate 80 which had been previous acidified with ascorbic acid to a pH of 4.0. This was followed by the slow addition of 4.27 g of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was transferred to a pressurized vessel and filtered through a 0.22 µm sterilizing membrane, in a sterile environment under pressure, and then filled in vials using customary procedures. The solution thus obtained was shown to be stable for 24 months when stored at temperatures between 2 and 8° C.

EXAMPLE 14

Process for the preparation of a stable and sterile solution of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in previously acidified polysorbate 80 (using a stainless steel reactor)

In a stainless steel reactor equipped with an internal agitation system, under an atmosphere of $N_2$ was added 100 mL of polysorbate 80 which had been previous acidified with ascorbic acid to a pH of 3.0. This was followed by the slow addition of 4.27 g of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was filtered through a 0.22 µm sterilizing membrane coupled to the reactor, in a sterile environment under pressure, and then filled in vials using customary procedures. The solution thus obtained was shown to be stable for 24 months when stored at temperatures between 2 and 8° C.

EXAMPLE 15

Process for the preparation of a stable and sterile solution of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate in posteriorly acidified polysorbate 80 (with compressed air agitation)

In a beaker equipped with a helical compressed air agitator, under an atmosphere of $N_2$ was added 100 mL of polysorbate 80. This was followed by the slow addition of 4.27 g of the tri-hydrate of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate. Agitation was maintained until complete solubilization of the active ingredient. The resulting solution was then acidified with ascorbic acid to a pH of 4.0. The resulting solution was transferred to a pressurized vessel and filtered through a 0.22 µm sterilizing membrane, in a sterile environment under pressure, and then filled in vials using customary procedures. The solution thus obtained was shown to be stable for 24 months when stored at temperatures between 2 and 8° C.

EXAMPLE 16

Process for the preparation of a stable and sterile solution of 4-acetoxy-2-a-benzoyloxy-5-ss-20-epoxy-1, 7ss-10-ss-tri-hydroxy-9-oxo-tax-11-en-13a-yl (2R,3S) 3-benzoylamino-2-hydroxy-3-phenylpropionate (II) in polysorbate 80 (with compressed air agitation)

In a beaker equipped with a helical compressed air agitator, under an atmosphere of $N_2$ was added 100 mL of polysorbate 80. This was followed by the slow addition of 0.6 g anhydrous 4-acetoxy-2-α-benzoyloxy-5-(3-20-epoxy-1,7β-10-β-tri-hydroxy-9-oxo-tax-11-en-13α-yl (2R,3S) 3-benzoylamino-2-hydroxy-3-phenylpropionate (II). Agitation was maintained until complete solubilization of the active ingredient. The resulting solution was transferred to a pressurized vessel and filtered through a 0.22 µm sterilizing membrane, in a sterile environment under pressure, and then filled in vials using customary procedures. The solution thus obtained was shown to be stable for 18 months when stored at temperatures between 2 and 8° C.

EXAMPLE 17

Process for the preparation of a stable and sterile solution of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II) in polysorbate 80 (using a stainless steel reactor)

In a stainless steel reactor equipped with an internal agitation system, under an atmosphere of N2 was added 100 mL of polysorbate 80. This was followed by the slow addition of 0.6 g of anhydrous 4-acetoxy-2-α-benzoyloxy-5-β-20-epoxy-1, 7β-10-β-tri-hydroxy-9-oxo-tax-11-en-13α-yl (2R,3S) 3-benzoylamino-2-hydroxy-3-phenylpropionate. Agitation was maintained until complete solubilization of the active ingredient. The resulting solution was filtered through a 0.22 µm sterilizing membrane coupled to the reactor, in a sterile environment under pressure, and then filled in vials customary procedures. The solution thus obtained was shown to be stable for 18 months when stored at temperatures between 2 and 8° C.

EXAMPLE 18

Process for the preparation of a stable and sterile solution of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II) in previously acidified polysorbate 80 (with compressed air agitation)

In a beaker equipped with a helical compressed air agitator, under an atmosphere of $N_2$ was added 100 mL of polysorbate 80 which had been previous acidified with ascorbic acid to a pH between 3.5 and 4.5. This was followed by the slow addition of 0.60 g of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate.

Agitation was maintained until complete solubilization of the active ingredient. The resulting solution was transferred to a pressurized vessel and filtered through a 0.22 μm sterilized membrane, in a sterile environment under pressure, and then filled in vials using customary procedures. The solution thus obtained was shown to be stable for 24 months when stored at temperatures between 2 and 8° C.

EXAMPLE 19

Process for the preparation of a stable and sterile solution of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II) in previously acidified polysorbate 80 (using a stainless steel reactor)

In a stainless steel reactor equipped with an internal agitation system, under an atmosphere of $N_2$ was added 100 mL of polysorbate 80 which had been previous acidified with ascorbic acid to a pH between 3.5 and 4.5.

This was followed by the slow addition of 0.60 g of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate. Agitation was maintained until complete solubilization of the active ingredient. The resulting solution was filtered through a 0.22 μm sterilizing membrane coupled to the reactor, in a sterile environment under pressure, and then filled in vials using customary procedures. The solution thus obtained was shown to be stable for 24 months when stored at temperatures between 2 and 8° C.

EXAMPLE 20

Process for the preparation of a stable and sterile solution of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate (II) in posteriorly acidified polysorbate 80 (with compressed air agitation)

In a beaker equipped with a helical compressed air agitator, under an atmosphere of $N_2$ was added 100 mL of polysorbate 80. This was followed by the slow addition of 0.60 g of 4-acetoxy-2-α-benzoyloxy-5-β-20-epoxy-1,7β-10-β-tri-hydroxy-9-oxo-tax-11-en-13α-yl (2R,3S) 3-benzoylamino-2-hydroxy-3-phenylpropionate. Agitation was maintained until complete solubilization of the active ingredient. The resulting solution was acidified with ascorbic acid to a pH between 3.5 and 4.5 and then transferred to a pressurized vessel and filtered through a 0.22 μm sterilizing membrane, in a sterile environment under pressure, and then filled in vials using customary procedures. The solution thus obtained was shown to be stable for 24 months when stored at temperatures between 2 and 8° C.

EXAMPLE 21

Comparative stability study between the tri-hydrate and anhydrous forms of (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate

| Time (months) | A % Docetaxel (tri-hydrate)[1] | A % Impurities (unknown) | Assay $(H_2O)$[2] | A % Docetaxel (anhydrous)[3] | A % Impurities (unknown) | Assay $H_2O$ |
|---|---|---|---|---|---|---|
| 0 | 99.51 | 0.49 | 6.32 | 99.28 | 0.72 | 0.10 |
| 3 | 99.23 | 0.77 | 6.35 | 99.21 | 0.79 | 0.11 |
| 6 | 99.30 | 0.70 | 6.21 | 99.26 | 0.73 | 0.12 |
| 12 | 98.91 | 1.09 | 6.42 | 98.93 | 1.07 | 0.09 |
| 18 | 98.72 | 1.28 | 6.31 | 98.65 | 1.35 | 0.12 |
| 24 | 98.21 | 1.79 | 6.29 | 98.29 | 1.71 | 0.13 |

Experimental data obtained in the laboratories of Quiral Quimica do Brasil S/A
[1]Prepared in the laboratories of Quiral Quimica do Brasil S/A.
[2]Water determined by Karl Fischer titration.
[3]Prepared according to EXAMPLE 2

Analysis was realized by HPLC using a Waters Spherisorb® C-18, 250×5 mm column, mobile phase MeOH:$H_2O$ 85:15, flow 1.5 mL/min. Related impurities reported as A% discounting the peak due to the dead volume. Samples were stored in amber glass vials under $N_2$ in a dessicator over $P_2O_5$ maintained between −5 and 0° C.

The example given in the present patent application are for illustrative purposes only and should not be construed as limiting the scope of the invention. Variations of the heretofore described processes which produce similar results will be apparent to persons skilled in the art.

The invention claimed is:

1. A process for the preparation of a concentrated pharmaceutical composition of docetaxel comprising the following steps:
   a) obtaining an anhydrous form of docetaxel in which the water content is from 0.08 to 0.12% w/w, by the substeps:
      a)(i) the hydrated docetaxel, in a solvent or in a chemically inert solvent mixture that forms an azeotrope with water and is of sufficient polarity to effect complete solubilization of the docetaxel, said solvent being selected from the group consisting of linear or branched alcohols, organic acids, halogenated solvents, and an aromatic solvent;
      a)(ii) removing the water of hydration contained in the mixture (i) by azeotropic distillation at a temperature between −20 and 40° C. and at a pressure between <0.001 and 800 mm Hg, until the water content is from 0.08 to 0.12% w/w;
   b) adding an acid, selected from the group consisting of tartaric acid, ascorbic acid, citric acid and acetic acid to polysorbate 80, under an atmosphere of nitrogen, in a sufficient quantity to adjust the pH in the range of 3.0 to 6.5;
   c) slowly adding anhydrous solid docetaxel, obtained by the process comprising a)(i) and a)(ii) and from which alcoholic solvents have been removed, to the resulting solution of the step (B), under agitation and a nitrogen atmosphere, until the docetaxel is completely solubilized and a transparent solution is formed, in which the concentration of the docetaxel in its anhydrous form in the polysorbate 80, is in the range from 1 to 100 mg/ml; and d) filtering the concentrated solution obtained in c) by passage through a sterilizing membrane having a porosity from 0.22 to 0.45 µm, to obtain a concentrated pharmaceutical composition of docetaxel.

2. The process according to claim 1 wherein an anhydrous solvent or a mixture of solvents is used in steps a)(i) and a)(ii).

3. The process according to claim 1 wherein the solvents employed in the steps a)(i) and a)(ii) are a short chain linear or branched alcohol.

4. The process according to claim 3 wherein the solvent employed is a short chain linear or branched alcohol.

5. The process according to claim 4 wherein the alcohol employed is ethanol.

6. The process according to claim 1 where in the step a), the starting docetaxel form contains 0.13 to 6.27% w/w of water, the solvents employed in the steps a)(i) and a)(ii) are absolute ethanol and anhydrous toluene in a relative proportion of 1:9, and step a)(ii) is performed at a pressure between <0.001 and 100 mm Hg.

7. The process according to claim 1 wherein the docetaxel employed as raw material in step a) is (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, in its hydrated form, in which the amount of hydration water is 0.13 to 6.27% w/w.

8. The process according to claim 1 wherein the docetaxal employed as the raw material in step a) is (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate .3 $H_2O$, in which the amount of hydration water is 6.27% w/w.

9. The process according to claim 1 wherein the docetaxel obtained at the end of the step a) is (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, in which the water content is in the range of 0.08 to 0.12% w/w.

10. A process according to claim 1 wherein the final concentration obtained in the concentrated solution containing (2R,3S) 4-acetoxy-2-α-benzoyloxy-5β-20-epoxy-1,7-β-10-β-tri-hydroxy-9-oxo-tax-11-en-13α-yl 3-tert-butoxycarbonylamino-2-hydroxy-3-phenylpropionate, docetaxal, is from 1 to 100 mg of the active principle, on an anhydrous basis, for each mL of the polysorbate 80.

11. The process according to claim 1 wherein the acid is added to the polysorbate 80 in an amount effective to adjust the pH of the pharmaceutical formulation in the range from 3.0 to 4.5.

12. The process according to claim 1 wherein the acid is ascorbic acid.

13. The process according to claim 11 wherein the acid is ascorbic acid.

* * * * *